United States Patent [19]

Nuzzolo et al.

[11] Patent Number: 4,977,079

[45] Date of Patent: Dec. 11, 1990

[54] METHOD FOR THE DETERMINATION OF ANTI-P. FALCIPARUM SPOROZOITE ANTIBODIES IN HUMAN BLOOD

[75] Inventors: Carlo A. Nuzzolo, Rome; Adriano Bernardi, Monterotondo; Antonello Pessi, Rome; Antonio S. Verdini, Monterotondo, all of Italy

[73] Assignee: Eniricerche S.p.A., Milan, Italy

[21] Appl. No.: 134,229

[22] Filed: Dec. 17, 1987

[30] Foreign Application Priority Data

Dec. 23, 1986 [IT] Italy ................. 22817 A/86

[51] Int. Cl.$^5$ ............... G01N 33/535; G01N 33/543; G01N 33/566; G01N 33/569
[52] U.S. Cl. .......................... 435/7; 435/21; 435/28; 435/810; 435/947; 436/501; 436/518; 436/529; 436/530; 436/531; 436/544; 436/808; 436/828
[58] Field of Search ............ 435/7, 21, 28, 810, 435/947; 436/501, 518, 529, 530, 531, 544, 808, 828

[56] References Cited

U.S. PATENT DOCUMENTS

| | | | |
|---|---|---|---|
| 3,995,018 | 11/1976 | Sjöquist | 436/531 |
| 4,591,552 | 5/1986 | Neurath | 436/828 |
| 4,659,678 | 8/1987 | Forrest et al. | 436/828 |
| 4,707,357 | 11/1987 | Dame et al. | 530/327 |
| 4,843,146 | 6/1989 | Bernardi et al. | 530/324 |

FOREIGN PATENT DOCUMENTS 8601721 3/1986 PCT Int'l Appl. .

OTHER PUBLICATIONS

Kabakoff in Maggio, (Ed.), *Enzyme-Immunoassay*, CRC Press, Inc., Boca Raton, Fla., 1980, pp. 71–104.
Ullman et al. in Maggio, (Ed.), *Ibid*, pp. 105–107.
Voller, in Maggio,. (Ed.), *Ibid*, p. 181.
Nakane et al., *Journ. Histochem. Cytochem.*, 22, 1084–1091, 1974.
Zavala et al., *Journ. Immunol. Metho.*, 93, 55–61, 1986.
Saunders, in Nakamura et al., (Eds.), *Immunoassays in the Clinical Laboratory*, Alan R. Liss, Inc., New York, 1979, pp. 99–118.

*Primary Examiner*—Esther L. Kepplinger
*Assistant Examiner*—David A. Saunders
*Attorney, Agent, or Firm*—Hedman, Gibson, Costigan & Hoare

[57] ABSTRACT

An immunoenzimatic method is disclosed for the detection and the measurement of anti-P. falciparum sporzoite antibodies in human blood and/or in its derivatives, which operates with a synthetic antigen-enzyme conjugate capable of forming with the antisporozoite antibodies a stable antibody-synthetic antigen-enzyme complex, and one or more proteins absorbed and/or covalently linked to a solid support, which eagerly bind the antisporozoite antibody of said complex.

The method, thanks to its simpleness, specificity and rapidity, is particularly useful in epidemiologic investigations into malaria and into the efficacy of an antimalarial vaccine.

10 Claims, No Drawings

METHOD FOR THE DETERMINATION OF ANTI-P. FALCIPARUM SPOROZOITE ANTIBODIES IN HUMAN BLOOD

The present invention relates to a novel immunoenzymatic method for the diagnosis of malaria in human blood.

More particularly, the present invention relates to a method for detecting and measuring anti-P. falciparum sporozoite antibodies in human blood, serum and/or plasma.

Malaria represents one of the most serious parasitic diseases and strikes, each year, hundreds on millions of persons, above all, in the tropical regions of Asia, Africa and America, causing a high infantile mortality.

The etiologic agent of malaria is a protozoan belonging to genus Plasmodium, which is transmitted to man through the bite of Anopheles mosquito.

Among the hundreds of species of Plasmodium existing in nature, only four are pathogen for man: Plasmodium ovale, Plasmodium malariae, Plasmodium vivax and Plasmodium falciparum.

This latter, in particular, represents the most diffused species, and causes most of morbidity and mortality associated with malaria.

The determination of antisporozoite antibodies in blood of individuals suspected to be malariated constitutes an essential clinical parameter for the diagnosis of malaria, and the evaluation of the efficacy on an antimalarial vaccine.

Generally, the diagnosis of malarial infections is carried out by means of the examination under the microscope of blood, or by immunological methods based on measurements of fluorescence (IFA), of radioactivity (IRMA) and of enzymatic activity (EIA).

The microscopic analysis of blood is however difficult and unsuitable for an epidemiologic investigation, wherein hundreds of thousands of samples are examined.

Not much suitable result furthermore the immunologic methods IRMA and IFA which, besides requiring long operating times, are complicated by the many steps they require, and by the use of substances unstable and noxious for man.

Among the EIA immunoenzymatic methods, the most commonly used is the ELISA (Enzyme-Linked-ImmunoSorbentAssay) test, which comprises:

(a) fixing, by absorption, or by a covalent chemical bond, a natural or synthetic antigen to a solid support;

(b) blocking the residual sites on the support with a suitable protein;

(c) incubating the antigen bound to the support with the serum under investigation, and (d) adding, in succession, an anti-human immunoglobulin antibody bound to a detector enzyme, and a colourless substrate for the enzyme which, in case of positive reaction of the serum, yields a coloured product.

This test, although it makes it possible some of the drawbacks of IRMA and IFA methods to be overcome, by using stable and non-radioactive substances, requires however long operating times (approximately 6 hours) and the use of reactants, such as anti-immunoglobulin antibodies-enzyme, which can only be obtained by means of complex and expensive methods.

Thus, the need exists in the art for a rapid, cheap and sensitive diagnostic method, useful for a mass probing in the areas wherein malaria is endemic, or in the areas wherein an accurate control has to be carried out in order to prevent and localize infective focuses.

Said need is fulfilled, according to the present invention, according to a new immunoenzymatic method which operates with a synthetic antigen-enzyme conjugate, capable of forming, with the antisporoize antibodies, a stable antibody-antigen-enzyme complex, and with the proteins which eagerly bind the antisporozoite antibody of said complex.

Therefore, a purpose of the present invention is an immunoenzymatic method for the detection and measurement of anti-P. falciparum sporozoite antibodies in samples of human blood and/or its derivatives, which comprises: incubating said samples in the presence of a synthetic antigen-enzyme conjugate capable of forming with the antisporozoite antibodies a stable antibody-synthetic antigen-enzyme complex; binding the antisporozoite antibody of said complex with the proteins either adsorbed on and/or covalently bound to, a solid support; and, finally determining the enzymatic activity of the complex bound to the proteins by means of the addition of a colourless enzymatic substrate capable of yielding, in case of positivity, a coloured product.

A further purpose of the present invention is the use of said synthetic antigen-detector enzyme conjugate for the preparation of a kit for the diagnosis of malaria.

Further purposes of the present invention will result evident from the reading of the disclosure and of the Examples.

The synthetic antigen-enzyme conjugate, suitable for the method according to the present invention, is formed by a sequential polypeptide, capable of recognizing and binding the antisporozoite antibodies, and by an enzyme.

In particular, according to the present invention, the sequential polypeptide is $(Asn-Ala-Asn-Pro)_n$, wherein n has a value comprised within the range of from 3 to 40, preferably of from 10 to 20, and exactly reproduces the polypeptidic segment of the natural circumsporozoitoize protein of the membrane of the sporozoite of P. falciparum.

The presence, in said polypeptide, of only two end functional chemical groups, $NH_2$ and COOH, renders it particularly suitable for the preparation of the conjugate according to the present invention, in as much as it makes it possible a stable covalent bond to be formed between the polypeptide and the enzyme, without being prejudicial to the catalytic activity of the same enzyme.

Said polypeptide is prepared in pure form, and with a high yield, according to the process disclosed in European Patatent Appln. Publication No. 209 643 by means of the polymerization of HCl.H-Asn-Ala-Asn-Pro-OPCP polypeptide, in an inert polar solvent, in the presence of a tertiary organic base.

Enzymes useful for the preparation of the conjugate of the present invention are selected from those capable of acting on a chromogen substrate. Examples for such enzymes are peroxidase, α-galactosidase and/or alkaline phosphatase. Preferably, peroxidase is used.

According to the present invention, the synthetic antigen-enzyme conjugate is prepared by means of a process comprising:

(1) oxidating the purified enzyme in a 0.1 M solution of $NaHCO_3$, such as, e.g., sodium metaperiodate, at room temperature (20°–25° C.), in the dark, for approximately 2 hours;

(2) adding to said solution the polypeptide dissolved in NaHCO$_3$ (pH 9.2) in a polypeptide/enzyme molar ratio of approximately 40/1, and keeping the resulting solution standing at room temperature, in the dark, for approximately 16 hours;

(3) adding to the obtained solution a reducing agent, such as, e.g., NaBH$_4$, and, finally (4) separating the polypeptide-enzyme conjugate.

In particular, according to a form of practical embodiment of the present invention, a conjugate is prepared wherein the polypeptide is (Asn-Ala-Asn-Pro)$_{17}$ and the enzyme is peroxidase. The conjugation degree, i.e., the molar ratio of the polypeptide to enzyme in said conjugate, is of 0.9–0.92, close to the expected value (1) for the pure conjugate.

The specific activity of peroxidase, determined by spectrophotometry at 405 nm as reported by H. Galloti (1979), J. Clin. Chem. Clin. Biochem. 17, 1–7, is 75% of that of the not conjugated enzyme.

In accordance with the method of the present invention, said conjugate is incubated, in a buffer solution, for approximately 20–30 minutes, with a sample of whole human blood, human serum or human plasma.

The reaction mixture is then incubated for a further 20–30 minutes on a solid support on which the Protein A is adsorbed and/or covalently bound.

Said protein is known to eagerly bind the human immunoglobulins, except for IgM and IgG$_3$, and hence forms with the antisporozoite antibody linked to the antigenenzyme conjugate, a stable complex.

Solid supports useful for the method according to the present invention are polysaccharide materials, such as cellulose and agarose, and plastics materials.

At the end of the reaction, and after suitable washings, to the mixtures a solution is added, which contains the chromogen enzymatic substrate and H$_2$O$_2$, and after 2–3 minutes, the development of colour is observed.

In case whole blood is analysed, the initial mixture, before being added to the Protein A, is centrifuged or filtered, in order to remove the suspended matter.

The threshold value, i.e., the minimum amount of positive serum which generates a colour development visible by the naked eye was respectively equal to 0.1 μl and 0.4 μl for two investigated sera.

Furthermore, no colour development is observed for the blank, which is constituted by the mixture containing the conjugate without the sample of blood and/or its derivatives, for serum and plasma of healthy persons, for non-malariated whole blood, either haemolysed or not, and for γ-globulins (Globuman - Bern).

This indicates a complete absence of interferences in the method according to the present invention.

The possibility of a rapid running, approximately 60 minutes, as compared to the 6 hours neeeded by the ELISA test, and the use of a small number of reactants, i.e., the antigen-enzyme and the proteins only, constitute a particular advantage of the method according to the present invention.

A considerable advantage of said method consists, furthermore, in the possibility of determining and measuring the antisporozoite antibodies in whole blood. This is due to the high stability of the conjugate of the present invention, as compared to the proteases contained in blood.

Furthermore, the method according to the present invention is absolutely specific, in fact, all samples which were found to be positive on IRMA, IFA and ELISA tests, when were analysed by means of the present method, confirmed their positivity.

Therefore, the method according to the present invention is particularly suitable for an epidemiologic study of malaria and, in particular, for the mass probing of malarial infection in areas lacking in sanitary units and structures.

The following experimental Examples are illustrative and non limitative of the same invention.

EXAMPLE 1

Preparation of (Asn-Ala-Asn-Pro)$_{17}$-Peroxidase Conjugate

Peroxidase enzyme (Sigma) was purified and freezedried before being conjugated with the peptide.

10 mg of pure enzyme (E) was then dissolved in 1 ml of 0.1 M NaHCO$_3$, and oxydated with 1 ml of 16 mM NaIO$_4$ (sodium metaperiodate), at room temperature (20°–25° C.), in the dark, for 2 hours.

At the end of said time period, to the reaction mixture 1 ml was added of NaHCO$_3$ (pH 9.2) containing 70 mg of (Asn-Ala-Asn-Pro)$_{17}$ peptide (P) in a molecular ratio of peptide/enzyme equal to 40/1.

The so-obtained mixture was quantitatively transferred inside a Pasteur pipette, closed at its end with glass wool, and to it 500 mg of Sephadex ® G-25 (Pharmacia Uppsala) powder was added; the pipette was then kept standing at room temperature, in the dark, for a further 16 hours.

To the reaction mixture, eluted from the pipette, 150 μl was added of 0.1 mM NaOH, containing 5 mg/ml of NaBH$_4$ and, 30 minutes later, to it, 450 μl of the same solution was added.

After approximately 1 hour, the mixture containing the enzyme-peptide conjugate (E-P) and the unreacted peptide (P) and enzyme (E), was equilibrated with 5 mM sodium acetate buffer, pH 4.4, in a column of Sephadex G-10, previously equilibrated with the same buffer. The mixture was then charged to a column (0.9×10 cm) of carboxymethyl-cellulose (CM-cellulose) equilibrated with 5 mM sodium acetate buffer, pH 4.4, and was eluted with 65 mM sodium acetate buffer, pH 4.4, and de-salified on Sephadex G10 column equilibrated with distilled water. The eluate containing the E-P compound, and the unreacted enzyme was freeze-dried.

The unreacted peptide was previously eluted with the charging buffer, and its integrity was analysed by I. R. spectroscopy.

The results obtained showed a same spectrum for the eluted peptide, and for the peptide used as the raw material. Thus, it was possible to conclude that no alterations had occurred in the peptide during the conjugation reaction and that the peptide bound to the enzyme was hence undamaged.

The degree of E-P conjugation, i.e., the molar ratio of the peptide to the enzyme in the conjugate, was determined by computing the increase in Asn, Ala and Pro aminoacid residues in the mixture containing E-P+free E, relatively to the initial enzyme E.

The analysis of the aminoacids was carried out, after acidic hydrolysis of E-P+E and E with 6N HCl at 100° C., for 24 hours, inside sealed ampouls, by means of a Beckman automatic aminoacid analyser.

In as much as the aminoacidic composition of the two peroxidasic isoenzymes (B and C) present in initial E, is known (Shannan L. M. et al., 1966, J. Biol. Chem. 241, 2,166), it was possible to compute, for an E:P molecular ratio of 1, corresponding to pure E-P conjugate, a theoretical increase in Asp, Ala and Pro, of respectively 63%, 68% and 100%.

For the above said aminoacids, increments of 58%, 62% and 90% were found, which correspond to to an E:P molar ratio of 0.90–0.92, approximately equivalent to the computed ratio for the pure conjugate.

The residual specific activity of peroxidase enzyme bonded to the peptide, determined by spectrophotometry at 405 nm with 1.7 nM ABTS (2,2'-azino-di(3-ethyl-benzothiazolyl-sulphonic acid)) and 0.83 mM $H_2O_2$ in 50 mM phosphate buffer, pH 6.0 (H. Gallati, J. Clin. Chem. Clin. Biochem. 17, 1–7, 1979) was approximately equal to 75% of that of the initial enzyme.

EXAMPLE 2

For this test, 8 malariated sera, the heparinized plasma of four healthy donors, the serum of 3 healthy persons and a sample of malariated whole blood were used, by mixing, in 1:1 volume ratio, the malariated serum with the haemolysed and not-haemolysed whole blood of a healthy person.

To 100 μl of 10mM phosphate buffer, pH 7.5, containing 0.15 M NaCl, 0.05% of Tween-20 (PBS-T) and 200 ng of E-P conjugate, added was: from 1 to 5 μl of blood, or plasma, or serum of healthy persons; or 10 μl of PBS-T respectively containing 0.05; 0.1; 0.2; 0.4; 0.8; 1.6; 3.2 μl of serum from malariated persons.

The solutions were kept standing at room temperature for 15–20 minutes.

In case of whole blood, the solution was centrifuged, or filtered, in order to remove the suspended matter.

Subsequently, said solutions were transferred inside colourless and transparent micropipette tips of plastics material, containing, at their end, glass wool and, on this, a bed consisting of an amount of approximately 6 μl of Protein A-Sepharose CL-4B (Pharmacia Uppsala), prewashed with PBS-T.

The solutions were percolated, by gravity, during a time of 20–30 minutes, the micro-columns were washed 3 times with 200 μl each time of PBS-T and twice with 200 μl each time of PBS (the buffer without Tween-20).

Subsequently, to each microcolumn, 200 μl was added of a substrate solution of 4-chloro-1-naphthol (Biorad) and $H_2O_2$, prepared by mixing, at use time, 1 part by volume of 4-chloro-1-naphthol (Biorad) (3 mg/ml in cold methanol) and 5 parts by volume of a solution of 6 μl of $H_2O_2$ at 30% (v/v) added to 10 ml of PBS. After 2–3 minutes, the development was observed of a deep blue colour for the positive samples.

The threshold value, i.e., the minimum amount of positive serum which generated an easily visible blue band, resulted of 0.1 μl –0.4 μl for two tested positive sera.

The specificity of the test was verified on a positive malariated serum (development of a blue band with E-P), using, in a test, 200 ng of free enzyme without E-P; in another test, a large excess (3 μg) (approximately 100 times) of free P in competition with the present E-P conjugate (200 ng).

At the end of the reaction, no colour development was observed.

No colour development was furthemore observed in the microcolumn, for the blank, formed by the reaction mixture with E-P without the addition of blood, serum or plasma; for the serum or plasma of healthy persons; for the non-malariated whole blood; or for human γ-globulins (Globuman - Bern) tested in an amount equivalent to about 6 μl of serum.

This indicated a complete absence of interferences in the test using the E-P conjugate.

The stability of peroxidase enzyme bound to the peptide (E-P) was determined by spectophotometric way, by carrying out drawings, at times ranging from 0 to 2 hours, from a solution of PBS-T (100 μl) containing 200 ng of E-P, to which samples of serum or plasma were added.

After 2 hours, the obtained results showed an unchanged peroxidasic activity.

What is claimed is:

1. Immunoenzymatic (EIA) method for detecting anti-P. falciparum sporozoite antibodies in human blood, serum or plasma, comprising:
   (a) incubating a human blood, serum, or plasma sample in the presence of the synthetic antigen-enzyme conjugate:
      (Asn-Ala-Asn-Pro)$_n$-E wherein n is an integer from 17 to 40 and E is an enzyme capable of yielding a colorimetric reaction with a specific substrate and wherein said conjugate is capable of forming with any sporozoite antibody the stable complex Ab-(Asn-Ala-Asn-Pro)$_n$-E without deactivating the enzyme activity;
   (b) subsequently incubating the sample of step (a) with a solid support which has adsorbed on it Protein-A capable of binding said antibody of said complex, and
   (c) determining the enzymatic activity of the complex bound to Protein-A by adding a colorless enzymatic substrate for said enzyme capable of yielding a colored product if antibodies are present in said sample.

2. Method according to claim 1, wherein the enzyme is peroxidase or alkaline phosphatase.

3. Method according to claim 1, wherein the conjugate is prepared by reacting in homogeneous phase in $NaHCO_3$, at room temperature (20°–25° C.), in the dark, an oxidated enzyme with a molar excess of (Asn-Ala-Asn-Pro)$_n$ polypeptide, wherein n is an integer from 17 to 40.

4. Method according to claim 3, wherein the molar ratio of the polypeptide to the enzyme in the conjugate is equal to, or approximately equal to, 0.92.

5. Method according to claim 1, wherein in the (a) step, the reaction is carried out at room temperature (20°–25° C.), for a reaction time of from 15 to 20 minutes.

6. Method according to claim 1, wherein the solid support is a polysaccharide or plastic material.

7. Method according to claim 1, wherein the support is cellulose or agarose.

8. Method according to claim 1, wherein in the (b) step, the reaction is carried out at room temperature (20°–25° C.), for a reaction time of from 20 to 30 minutes.

9. Method according to claim 1 wherein n is 20.

10. Diagnostic Kit for the determination and measurement of anti-P. falciparum sporozoite antibodies comprising the synthetic antigen-enzyme conjugate and the solid support with adsorbed Protein A, both as defined in claim 1.

* * * * *